(12) United States Patent
Davis, III

(10) Patent No.: US 9,782,286 B2
(45) Date of Patent: Oct. 10, 2017

(54) FULL BODY ELEVATOR

(76) Inventor: Thomas W. Davis, III, Bethany, LA (US)

( * ) Notice: Subject to any disclaimer, the term of this patent is extended or adjusted under 35 U.S.C. 154(b) by 1241 days.

(21) Appl. No.: 13/421,139

(22) Filed: Mar. 15, 2012

(65) Prior Publication Data

US 2012/0233783 A1    Sep. 20, 2012

Related U.S. Application Data

(63) Continuation-in-part of application No. 12/380,694, filed on Mar. 3, 2009, now abandoned.

(60) Provisional application No. 61/068,077, filed on Mar. 4, 2008.

(51) Int. Cl.
    *A61F 5/01*     (2006.01)
    *A61F 5/34*     (2006.01)

(52) U.S. Cl.
    CPC ............... *A61F 5/012* (2013.01); *A61F 5/34* (2013.01)

(58) Field of Classification Search
    CPC ..................................................... A61G 13/12
    USPC ... 5/454, 455, 644, 650, 648, 456, 600, 613, 5/614, 615, 689, 690, 706, 710, 652, 5/655.3; 128/845, 882, 95.1, 99.1, 117.1, 128/118.1, 112.1
    See application file for complete search history.

(56) References Cited

U.S. PATENT DOCUMENTS

| | | | | |
|---|---|---|---|---|
| 4,639,960 | A * | 2/1987 | Quillen et al. | 5/710 |
| 5,170,522 | A * | 12/1992 | Walker | 5/615 |
| 5,970,545 | A * | 10/1999 | Garman et al. | 5/644 |
| 8,181,295 | B1 * | 5/2012 | Mallinger | 5/710 |
| 8,261,387 | B2 * | 9/2012 | Lipman et al. | 5/709 |
| 2005/0278861 | A1 * | 12/2005 | Kasatshko | 5/713 |
| 2006/0021146 | A1 * | 2/2006 | Tokarz | 5/632 |

* cited by examiner

*Primary Examiner* — Tarla Patel
(74) *Attorney, Agent, or Firm* — R. Keith Harrison

(57) ABSTRACT

A full body elevator includes an inflatable upper body elevator having a sloped backrest panel and a generally flat, horizontal butt rest panel extending from the backrest panel; and an inflatable lower body elevator having a leg portion with a leg support panel sloping from the butt rest panel and a foot portion with a foot support panel selectively inflatable and extendable with respect to the leg portion.

20 Claims, 7 Drawing Sheets

FULL BODY ELEVATOR

CROSS-REFERENCE TO RELATED APPLICATIONS

This application is a continuation-in-part of parent U.S. application Ser. No. 12/380,694, filed Mar. 3, 2009 now abandoned and entitled LEG AND FEET ELEVATOR, which claims priority from U.S. provisional application No. 61/068,077, filed on Mar. 4, 2008 and entitled "LEG AND FEET ELEVATOR", which provisional application and parent application are hereby incorporated by reference herein in their entireties.

FIELD

Embodiments of the disclosure relate generally to recreational and therapeutic lounging. More particularly, the disclosure relates to a full body elevator which selectively elevates the upper body and the legs and feet of a user.

BACKGROUND

In most cases people lounge for either recreation or therapy, whichever the case may be proper lower body support is necessary. Consumers need to elevate their lower extremities for recreational and therapeutic needs when lounging both indoors and outdoors. Lounging in a semi-upright position without proper leg and foot support can cause various physical strains. It is accordingly an object of the present device to greatly increase the comfort of the consumer while adding lightweight and portable features that will result in the multi-positioning use of this device. Known devices for positioning include but are not limited to variations of supportive pillows of soft or in some cases beaded filling or memory foam wedges that do not provide the firm support surface, mobility, cost-efficiency and durability of this particular device.

Some known devices are larger foam wedges providing only one angle of elevation without the ability to move easily into different areas. There are wedges that are used strictly in medical professions for supporting the lower extremities or inclined mattresses—which are too expensive for the average consumer. This device has multiple positioning for the consumer due to its right angle triangle construction. The support of the leg and feet elevator relieves strain from the lower extremities when left hanging downward from lounging in a semi-upright position. Lounging in a semi-upright position can be less restrictive, comfortable and even prevent poor blood circulation to the legs when lying flat if the leg and feet elevator is applied.

Yet other known devices for lounging are recommended for use in one area or another, they are not portable and cannot be taken with you. What is commonly used in the home to position consumers in a lounging position are pillows and rolled up blankets to prop up the consumers leg and feet on flat or elevated mattresses or in non-adjustable seats.

In view of the foregoing, when in a semi-upright or flat position a device is needed for the support and comfortable positioning of the consumers leg and feet for recreational and therapeutic purposes. A device is also needed for the positioning of a consumer's leg and feet that will alleviate poor circulation, strains and pains of lounging in uncomfortable, unsupportive and unstable positions. This device is safe, portable, easy to use, lightweight and effective for therapeutic needs. It would further be desirable if the device also provides safe, easy, effective, accessible and comfortable positioning of the consumer's lower body, to facilitate effective air exchange and support for the leg and feet.

SUMMARY

Embodiments of the disclosure are generally directed to a full body elevator. An illustrative embodiment of the full body elevator includes an inflatable upper body elevator having a sloped backrest panel and a generally flat, horizontal butt rest panel extending from the backrest panel; and an inflatable lower body elevator having a leg portion with a leg support panel sloping from the butt rest panel and a foot portion with a foot support panel selectively inflatable and extendable with respect to the leg portion.

BRIEF DESCRIPTION OF THE DRAWINGS

The disclosure will now be made, by way of example, with reference to the accompanying drawings, in which like reference numerals refer to similar elements and.

Figure 1:
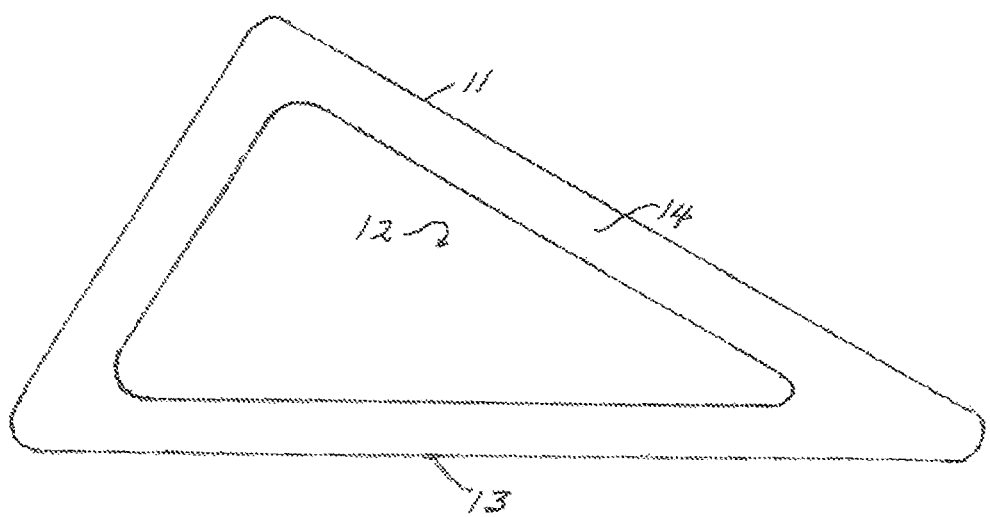
FIG. 1 shows a landscape/side view of the "Leg and Feet Elevator" and various components thereof.

Unless otherwise indicated illustrations in the figures are not necessarily drawn to scale.

DETAILED DESCRIPTION

The present device is best understood by reference to the detailed figures and description set forth herein.

Embodiments of the device are discussed below with reference to the FIGURES. However, those skilled in the art will readily appreciate that the detailed description given herein with respect to these figures is for explanatory purposes as the device extends beyond these limited embodiments.

A portable leg and feet elevator will be described in which the preferred embodiment combines a pneumatic cushion and hospital wedge designed at a right angle triangle for multi-positioning. It is to be understood that any exact measurements/dimensions or particular construction materials indicated herein are solely provided as examples of suitable configurations and are not intended to be limiting in any way. Depending on the needs of the particular application, those skilled in the art will readily recognize in light of the following teachings, a multiplicity of suitable alternatives implementation details. It is to be further understood that while many design features are described below in the context of complying with pertinent government regulations, alternative embodiments and application of the present may include corresponding design features that may be only partially or not at all in compliance, such non-compliant embodiments and applications of the present device are none the less within the scope of the present device. Likewise, al safety oriented design features are optional and may be replaced with any suitable implementation approach known to those skilled in the art.

It is contemplated that other embodiments of the present device may implement other suitable designs, depending upon the needs of the particular consumer, for example, without limitation, the base could be sloped, however, this embodiment places too much support on the lower extremities. This device is more suitable for anyone who likes lounging but prefers to do so in a semi-upright position with support for the legs and feet. This device is to be used for recreational and/or therapeutic purposes for older children up to adult and is not suitable to be used as a flotation device.

The entire device is portable and an outer covering wraps completely around the device to help prevent skin from sweating, sliding and accidental punctures or tears to the cushions. The device may be placed on the floor inside, outside, on the ground-concrete, grass or dirt. The measurements provided are for the preferred embodiments of the present device, and those skilled in the art, in light of the present teachings, will recognize that alternate measurements may also be suitable for a Leg and Feet Elevator.

The present embodiment is comprised of a type of plastic/rubberized plastic, vinyl, lightweight material suitable for inflation. This material can be made from a flame retardant, water-proof, non-breathable material that is mildew, proof, or covered with nonflammable, waterproof material. The device is preferably flame retardant, and meets pertinent government regulations; such as, without limitations, the NFPA 701 Flame Resistance and MIL-F-21840F shear strength requirements. The vinyl portions are preferably waterproof, tear resistant, rot resistant, and are in compliance with pertinent government regulations; such as, without limitation, NFPA 701 Flame Resistance and State of Louisiana F-222.03 Flame Retardant Rating.

FIG. 1 shows a landscape/side view of the "Leg and Feet Elevator", and various components thereof: Pneumatic cushions are used to design the present embodiment in an elevation of approximately 30×60×90 degrees in measurement. This right angle triangle design is created for support of the lower extremities and can be used for any recreational or therapeutic activity. The side panel 12 is connected to the rolled edge 14 of each side of the device to maintain the devices stability with respect to the heat sealed 13 rolled edge 14 and the outer cover 11 which conforms the devices shape because it wraps completely around the device and is provided for support and comfort to skin, reduction in sliding and easy care. The elevator of the present embodiment has an angle for comfort and prevention of pressure to the legs and feet. This embodiment is also more affordable than the aforementioned.

Figure 2:
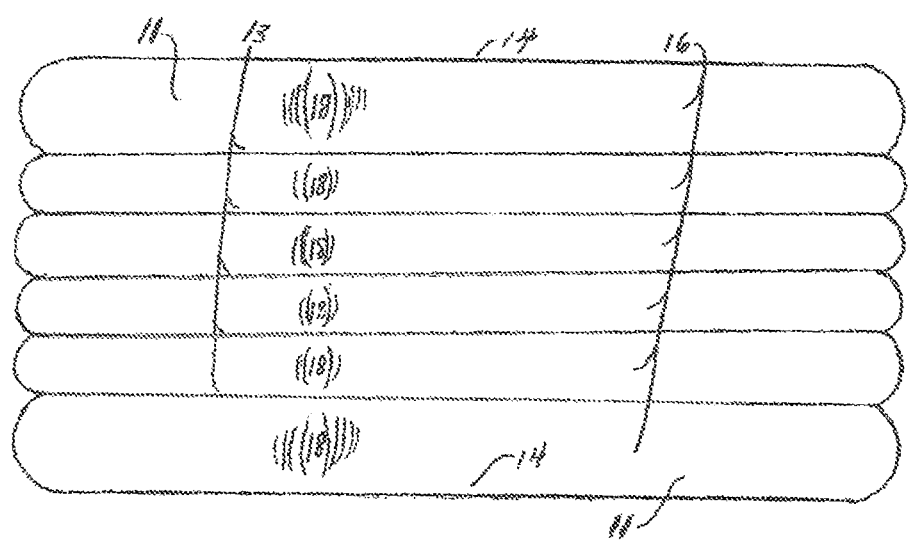
FIG. 2 shows a view from X-axis (above) of said embodiment. To give one a better understanding of said device.

FIG. 2 shows a view from the X-axis, (above) of said embodiment. To give a better understanding of said device there are several envelopes 16 formed between panels for necessary support of the lower extremities. Each envelope 16 is heat sealed 13 and encompassed by the rolled edge 14 for added support. At the apex of this device are indicator marks 18 to illustrate bends in the surface for a more contoured shape. The outer cover 11 wraps completely around the device and is constructed of a non-porous, vinyl/plastic, flame retardant material.

Figure 3:
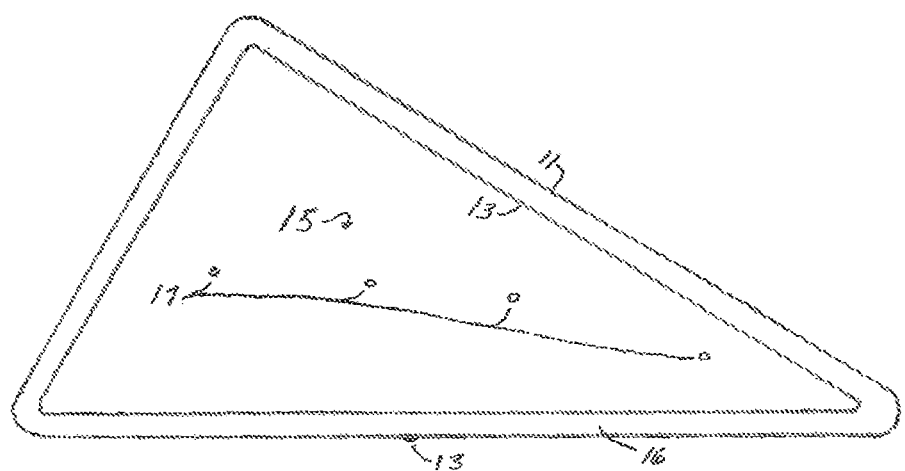
FIG. 3 shows a side view with cut-away section, showing the inner construction and parts.

FIG. 3 illustrates a side view with cut-away section showing the inner construction and parts; a view of the components of the elevating apparatus of an exemplary leg and feet elevator, in accordance with an embodiment of the present device. The inner panels 15 are equipped with air diffuser ports 17 which allow air to flow to and from the heat sealed 13 envelopes 16; the outer cover 11 is heat-sealed 13 as well for proper support for lounging comfortably.

Figure 4:
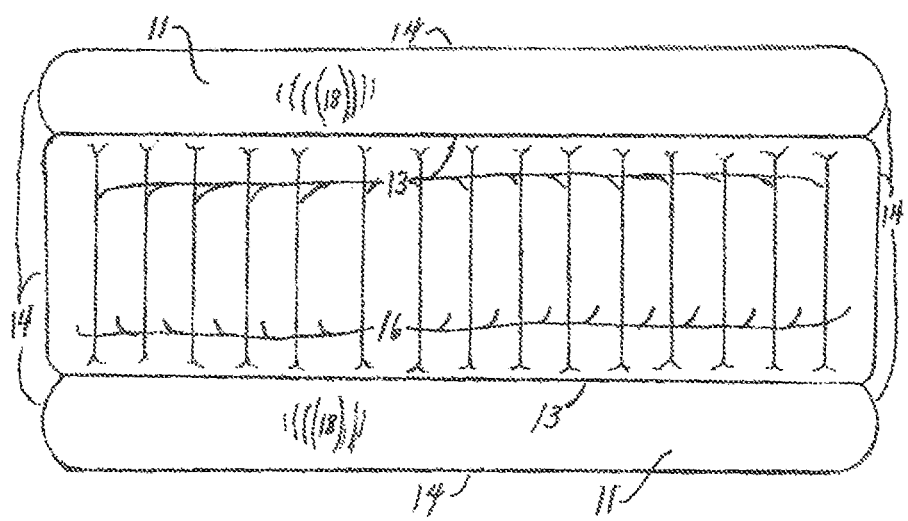
FIG. 4 shows a cut-away cross-section view at the apex.

FIG. 4 shows a cut-away cross-section view at the apex; the heat sealed 13 envelopes 16 that are formed between panels are encompassed by a rolled edge 14 on either end of the device. Indicator marks 18 at the apex illustrate bends in the surface. The outer cover 11 which is a waterproof, nonporous, mildew resistant material wraps around the device completely.

Figure 5:
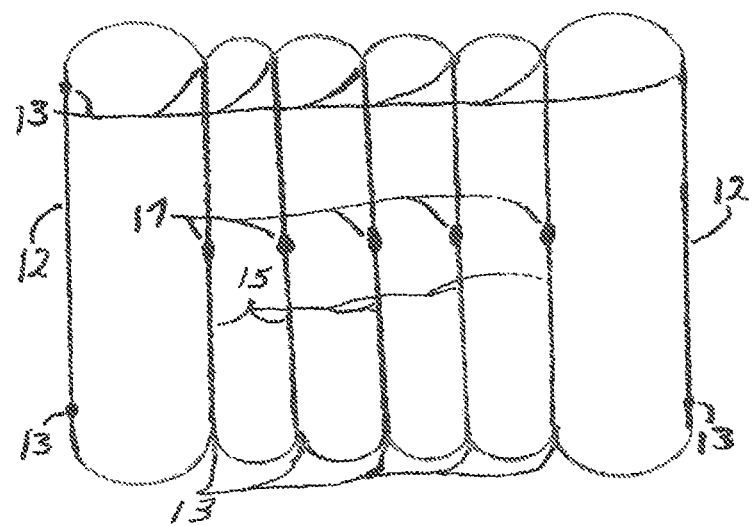
FIG. 5 shows a different construction configuration embodiment of the present device.

FIG. 5 shows a different construction configuration embodiment of the same device with a transverse or crossways tubular configuration. This view shows the heat sealed 13 inner panels 15 with air diffuser ports 17 between each inner panel. The heat sealed 13 side panels 12 encompass the inner panels 15 for added support.

Figure 6:
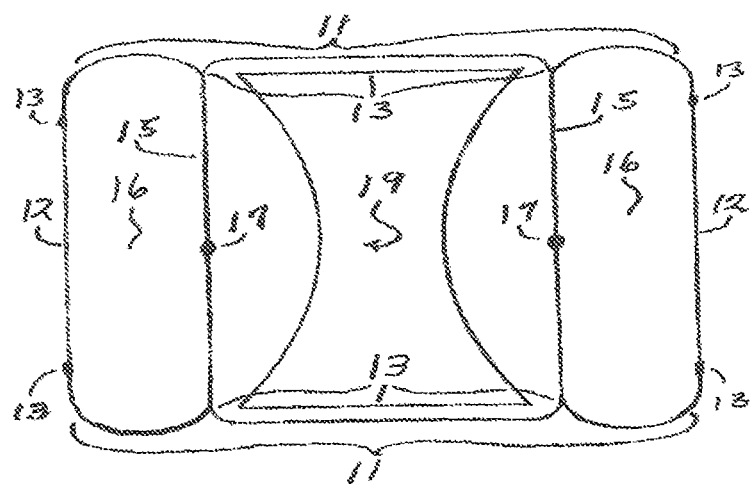
FIG. 6 shows an illustration of "FIG. 5" cross-section cut-away section and said components.

FIG. 6 shows FIG. 5 cross-section cut-away section and said component parts. Heat sealed 13 inner panels 19 are surrounded by air diffuser ports 17 which allow air to flow to and from the inner panels 15. The envelopes 16 formed between the panels are connected to the heat sealed 13 side panel 12 which are encompassed by the outer cover 11 that wraps completely around the right triangular shaped device.

The foregoing embodiments of the present device comprise a multiplicity of aspects, which, for the sake of clarity, are next highlighted separately by way of example and not limitation. For example, one aspect of the preferred embodiment of the present device is to provide elevation of the consumer's leg and feet with the use of an approximately 20-40 degree range to allow for comfortable, effective versatile positioning of the leg and feet.

Another aspect of the preferred embodiment of the present device is that it can be easily cleaned and meets most, if not all, sanitation needs for its repeated use. Another aspect of the preferred embodiment of the present device is that it is constructed of durable and waterproof materials.

Embodiments of the present device may be used in the home or outside the home for use by anyone who participates in recreational or therapeutic lounging.

Alternative embodiments cannot address cost reduction or regulatory issued for certain applications like this one.

Having fully described at least one embodiment of the present device, other equivalent or alternative methods of implementing a leg and feet elevator according to the present device will be apparent to those skilled in the art. The device has been described above by way of example, and the specific embodiments disclosed are not intended to limit the device to the particular forms disclosed. This device is thus to cover all modifications, equivalents and alternatives falling within the spirit and scope of the following claims.

Figure 7:
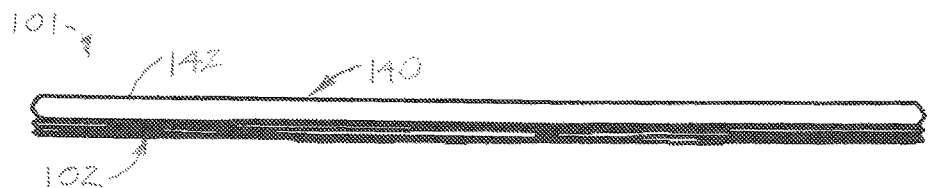
FIG. 7 is a side view of an illustrative embodiment of a full body elevator in a deflated configuration.
Figure 8:
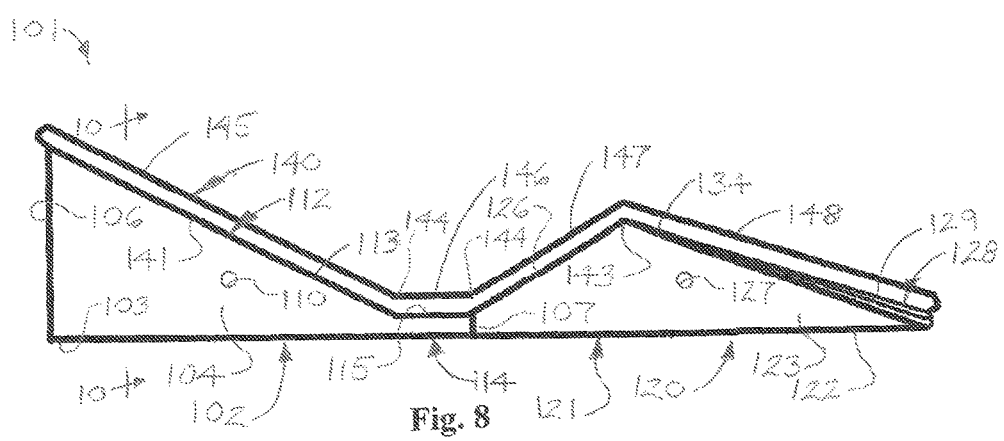
FIG. 8 is a side view of an illustrative embodiment of the full body elevator in a partially-inflated configuration.
Figure 9:
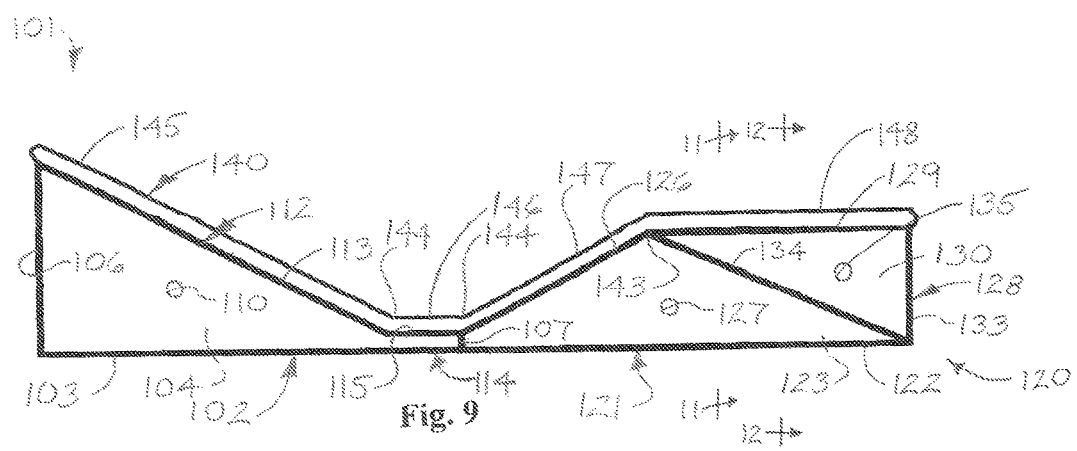
FIG. 9 is a side view of an illustrative embodiment of the full body elevator in a fully-inflated configuration.

Referring next to FIGS. 7-18 of the drawings, an illustrative embodiment of a full body elevator is generally indicated by reference numeral 101. As illustrated in FIGS. 8 and 9, the full body elevator 101 includes an upper body elevator 102 and a lower body elevator 120. In operation of the full body elevator 101, which will be hereinafter described, the upper body elevator 102 is selectively inflatable to elevate and support the upper body of a user (not illustrated) as the user lies on the full body elevator 101. The lower body elevator 120 is selectively inflatable to elevate and support the legs and feet (not illustrated) of the user as the user lies on the full body elevator 101. The full body elevator 101 may be fabricated of lightweight plastic sheets or panels such as plastic/rubberized plastic, vinyl and/or other lightweight material suitable for inflation and which are glued, heat-sealed and/or otherwise attached to each other in a pneumatically-sealable manner to form the inflatable upper body elevator 102 and lower body elevator 120, as will be hereinafter described.

Figure 10:
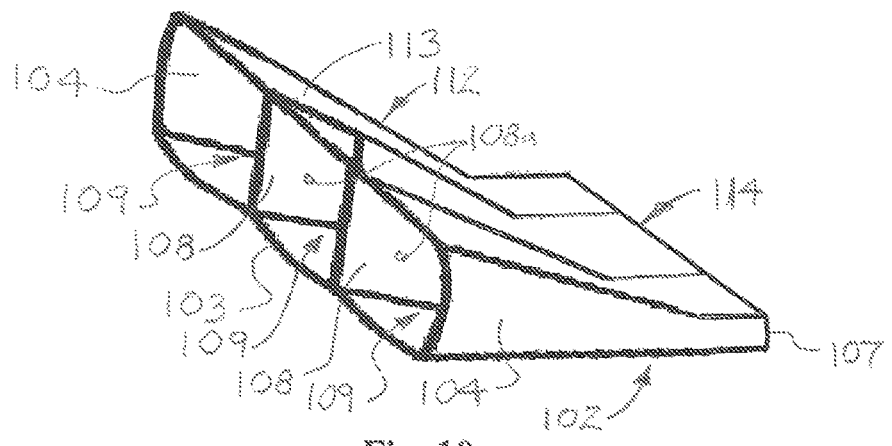
FIG. 10 is a perspective view, taken along section lines 10-10 in FIG. 8.

As illustrated in FIGS. 8-10, the upper body elevator 102 may include a backrest portion 112 and a butt rest portion 114 which extends from the backrest portion 112. The upper body elevator 102 has an upper body elevator bottom panel 103 which traverses the longitudinal dimension of the backrest portion 112 and the butt rest portion 114. In some embodiments, the upper body elevator bottom panel 103 may be generally rectangular, although in other embodiments the upper body elevator bottom panel 103 may have alternative shapes. A pair of generally spaced-apart, parallel upper body elevator side panels 104 may extend from opposite side edges of the upper body elevator bottom panel 103. As illustrated in FIGS. 8 and 9, in the inflated configuration of the upper body elevator 102, each upper body elevator side panel 104 may generally have the shape of a right triangle. An upper body elevator head end panel 106 may extend from the upper body elevator bottom panel 103 between the wide edges of the respective triangular upper body elevator side panels 104. An upper body elevator butt end panel 107 may extend from the upper body elevator bottom panel 103 between the narrow edges of the respective generally triangular upper body elevator side panels 104. A sloped backrest panel 113 may extend between the upper body elevator side panels 104 to the upper edge of the upper body elevator head panel 106. A generally flat or horizontal butt rest panel 115 may extend from the bottom portion of the backrest panel 113 to the upper body elevator butt end panel 107. The upper body elevator bottom panel 103, the upper body elevator head end panel 106, the upper body elevator butt end panel 107, the backrest panel 113 and the butt rest panel 115 may be attached to the upper body elevator side panels 104 via gluing, heat-sealing and/or other pneumatically-sealable method or technique known by those skilled in the art.

It will be recognized and understood that the foregoing description of the upper body elevator 102 is exemplary and that the upper body elevator 102 can be fabricated using a greater number or a lesser number of panels than the upper body elevator bottom panel 103, the upper body elevator side panels 104, the upper body elevator head panel 106, the upper body elevator butt panel 107, the backrest panel 113 and the butt rest panel 115. Moreover, in some embodiments, rather than being distinct or discrete panels, two or more of the upper body elevator bottom panel 103, the upper body elevator side panels 104, the upper body elevator head panel 106, the upper body elevator butt panel 107, the backrest panel 113 and the butt rest panel 115 can be combined to form a single panel according to the knowledge of those skilled in the art. Additionally, the panels may be continuous with one another and form the various faces of the upper body elevator 102 rather than being discrete panels.

As illustrated in FIG. 10, the upper body elevator 102 has at least one upper body elevator air compartment 109. Each upper body elevator air compartment 109 may extend a portion of or substantially the entire length of the upper body elevator 102. In some embodiments, at least one upper body elevator partition 108 may extend between the upper body elevator bottom panel 103 and the backrest panel 113, forming at least two adjacent upper body elevator air compartments 109 in the upper body elevator 102. In the illustrative embodiment illustrated in FIG. 10, a pair of spaced-apart upper body elevator partitions 108 extends between the upper body elevator bottom panel 103 and the backrest panel 113, forming three adjacent upper body elevator air compartments 109 in the upper body elevator 102. In other embodiments, three or more upper body elevator partitions 108 may extend between the upper body elevator bottom panel 103 and the backrest panel 113 to form four or more adjacent upper body elevator air compartments 109 in the upper body elevator 102. Each upper body elevator partition 108 may be attached to the upper body elevator bottom panel 103 and the upper body elevator backrest panel 113 via gluing, heat-sealing and/or other pneumatically-sealable method or technique known by those skilled in the art or may be fabricated in one piece with the panels 103, 113. At least one air diffuser 108a may extend through each upper body elevator partition 108 to facilitate flow of air between the adjacent upper body elevator air compartments 109.

As illustrated in FIGS. 8 and 9, an air inlet valve 110 is provided in the upper body elevator 102. The air inlet valve 110 is disposed in pneumatic communication with the upper body elevator air compartments 109 (FIG. 10) and is adapted for pneumatic connection to an air pump (not illustrated) which may be conventional, to facilitate selective inflation of the upper body elevator 102. In some embodiments, the air inlet valve 110 may be provided in one of the upper body elevator side panels 104, as illustrated. In other embodiments, the air inlet valve 110 may be provided in any other accessible location on the upper body elevator 102.

Figure 11:
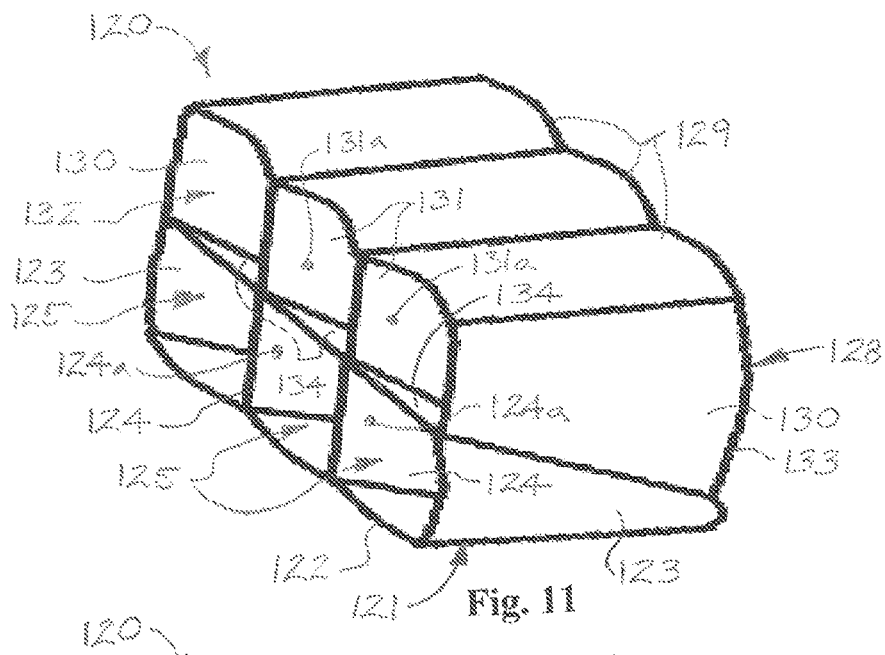
FIG. 11 is a perspective view, taken along section lines 11-11 in FIG. 9.
Figure 12:
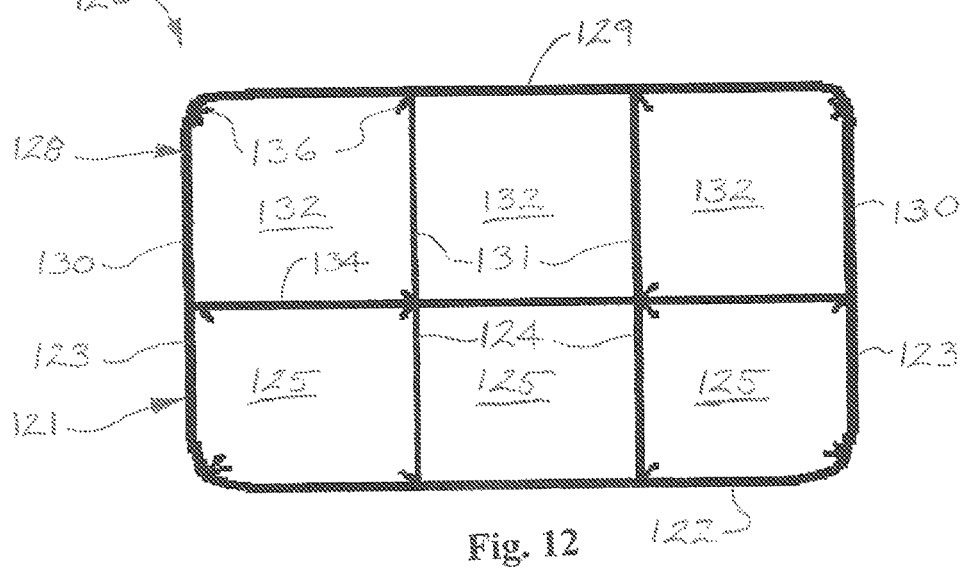
FIG. 12 is a perspective view, taken along section lines 12-12 in FIG. 9.
Figure 13:
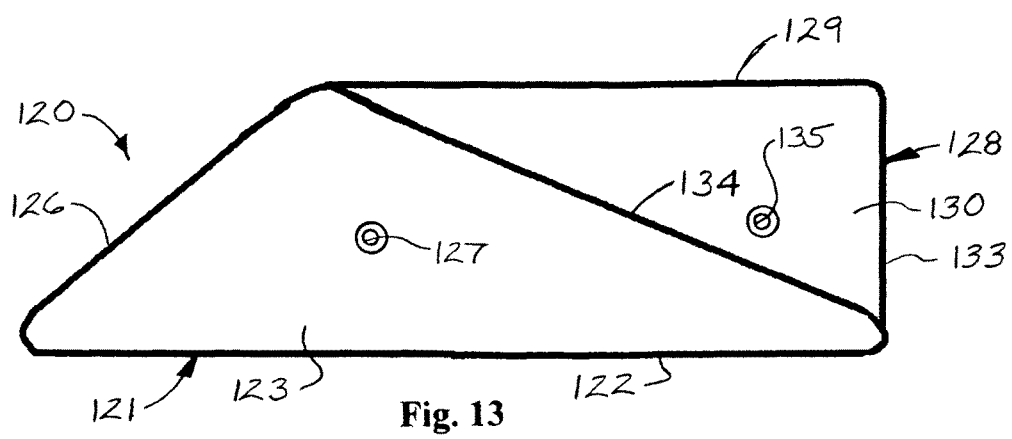
FIG. 13 is a side view of a lower body elevator of an illustrative embodiment of the full body elevator.
Figure 14:
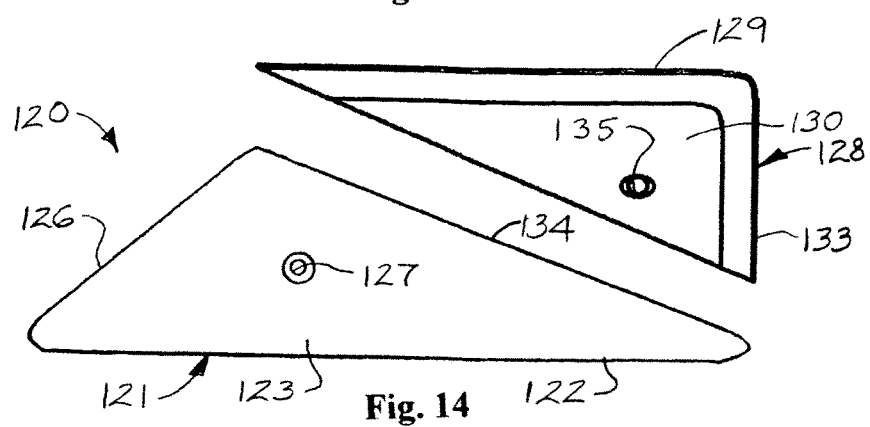
FIG. 14 is an exploded side view of the lower body elevator of an illustrative embodiment of the full body elevator.
Figure 15:
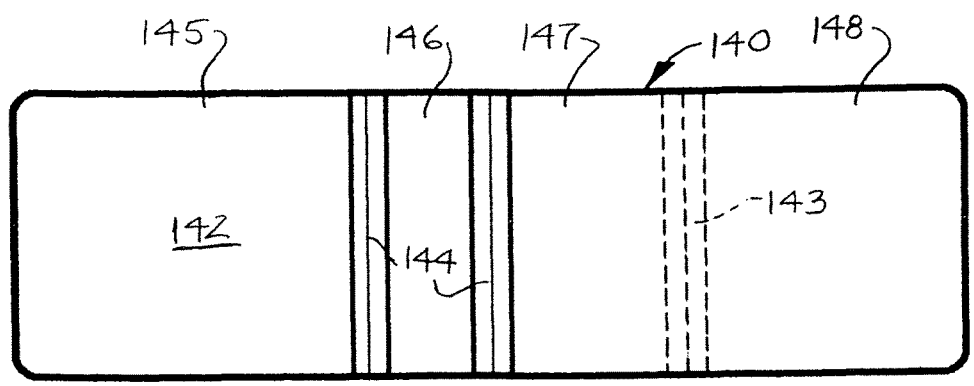
FIG. 15 is a top view of an elevator cushion of an illustrative embodiment of the full body elevator.
Figure 16:
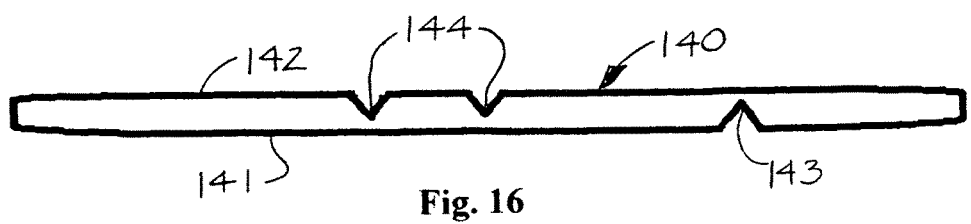
FIG. 16 is a side view of the elevator cushion.

As illustrated in FIGS. 8 and 9, the lower body elevator 120 extends from the upper body elevator 102 of the full body elevator 101. As illustrated in FIG. 9, the lower body elevator 120 of the full body elevator 101 may include a selectively inflatable leg portion 121 and a foot portion 128 which is selectively inflatable and extendable from the leg portion 121. In some embodiments, the leg portion 121 and the foot portion 128 may be separately inflatable. In other embodiments, the leg portion 121 and the foot portion 128 may be inflatable together. As illustrated in FIGS. 11 and 12, the leg portion 121 of the lower body elevator 120 may include a leg portion bottom panel 122. A pair of leg portion side panels 123 extend from opposite side edges of the leg portion bottom panel 122. In the inflated configuration of the leg portion 121, each leg portion side panel 123 may be generally shaped in the configuration of a scalene triangle. As illustrated in FIGS. 8 and 9, a sloped leg support panel 126 may extend along a first pair of edges of the leg portion side panels 123, adjacent to and upwardly-sloped from the butt rest panel 115 of the upper body elevator 102.

The foot portion 128 of the lower body elevator 120 may include a pair of spaced-apart foot portion side panels 130 which extend from the respective leg portion side panels 123 of the leg portion 121. A foot portion end panel 133 may extend between the foot portion side panels 130. A foot support panel 129 is provided on the foot portion side panels 130 and the foot portion end panel 133. As illustrated in FIG. 9, in the inflated configuration of the foot portion 128, each foot portion side panel 130 may be generally shaped in the configuration of a right triangle.

It will be recognized and understood that the foregoing description of the lower body elevator 120 is exemplary and that the lower body elevator 120 can be fabricated using a greater number or a lesser number of panels than the leg portion bottom panel 122, the leg portion side panels 123, the foot support panel 129 and the foot portion end panel 133. Moreover, in some embodiments, two or more of the leg portion bottom panel 122, the leg portion side panels 123, the foot support panel 129 and the foot portion end panel 133 can be combined to form a single panel rather than distinct or discrete panels according to the knowledge of those skilled in the art. Additionally, the panels may be continuous with one another and form the various faces of the lower body elevator 120 rather than being discrete panels.

As illustrated in FIG. 11, the leg portion 121 of the lower body elevator 120 has at least one leg portion air compartment 125. Each leg portion air compartment 125 may extend a portion of or substantially the entire length of the lower body elevator 120. The foot portion 128 of the lower body elevator 120 has at least one foot portion air compartment 132. Each foot portion air compartment 132 may extend a portion of or substantially the entire length of the foot portion 128. An air compartment divider 134 may separate the leg portion air compartment or compartments 125 in the leg portion 121 from the foot portion air compartment or compartments 132 in the foot portion 128. In some embodiments, at least one leg portion partition 124 may extend between the leg portion bottom panel 122 and the air compartment divider 134 to form at least two leg portion air compartments 125 in the leg portion 121. At least one air diffuser 124a may extend through each leg portion partition 124 to facilitate flow of air between the adjacent leg portion air compartments 125.

At least one foot portion partition 131 may extend between the air compartment divider 134 and the foot support panel 129 to form at least two adjacent foot portion air compartments 132 in the foot portion 128. In some embodiments, the foot portion air compartments 132 of the foot portion 128 may be pneumatically sealed from the leg portion air compartments 125 of the leg portion 121. In other embodiments, the foot portion air compartment 132 of the foot portion 128 may pneumatically communicate with the leg portion air compartments 125 of the leg portion 121 through at least one air diffuser (not illustrated) or the like. At least one air diffuser 131a may be provided in each foot portion partition 131 to facilitate flow of air between the adjacent foot portion air compartments 132.

As illustrated in FIG. 12, panel seals 136 may attach the leg portion bottom panel 122, the leg portion side panels 123, the leg portion partitions 124, the air compartment divider 134, the foot portion partitions 131, the foot portion side panels 130 and the foot support panel 129 to each other in the lower body elevator 120. The panel seals 136 may include but are not limited to gluing and heat sealing.

As illustrated in FIGS. 8 and 9, an air inlet valve 127 is provided in the leg portion 121 of the lower body elevator 120. The air inlet valve 127 is disposed in pneumatic communication with the leg portion air compartments 125 (FIG. 11) of the leg portion 121 and is adapted for pneumatic connection to an air pump (not illustrated), which may be conventional, to facilitate inflation of the leg portion 121. In some embodiments, the air inlet valve 127 may be provided in one of the leg portion side panels 123, as illustrated. In other embodiments, the air inlet valve 127 may be provided in any other accessible location on the leg portion 121.

As illustrated in FIG. 9, in embodiments in which the foot portion 128 is pneumatically sealed from the leg portion 121, an air inlet valve 135 is provided in the foot portion 128 of the lower body elevator 120. The air inlet valve 135 is disposed in pneumatic communication with the foot portion air compartments 132 (FIG. 11) of the foot portion 128 and is adapted for pneumatic connection to an air pump (not illustrated), which may be conventional, to facilitate inflation of the foot portion 128. In some embodiments, the air inlet valve 135 may be provided in one of the foot portion side panels 130, as illustrated. In other embodiments, the air inlet valve 135 may be provided in any other accessible location on the foot portion 128.

In some embodiments, the lower body elevator 120 may be attached to the upper body elevator 102 at the butt rest portion 114 via gluing, heat sealing and/or other attachment mechanism or the upper body elevator 102 and the lower body elevator 120 may be fabricated together in one piece. Accordingly, in either of those embodiments, the upper body elevator 102 and the lower body elevator 120 may be separately inflatable units. Thus, the upper body elevator butt end panel 107 may separate the upper body elevator air compartments 109 (FIG. 10) of the upper body elevator 102 from the leg portion air compartments 125 (FIG. 11) of the leg portion 121 and the foot portion air compartments 132 (FIG. 11) of the foot portion 128. Alternatively, in either of those embodiments, the upper body elevator 102 and the lower body elevator 120 may be pneumatically connected such that they are inflatable together. In still other embodiments, the upper body elevator 102 and the lower body elevator 120 may be physically separate units and therefore individually inflatable.

As illustrated in FIGS. 7-9, 15 and 16, in some embodiments, an elevator cushion 140 may be provided on the upper body elevator 102 and the lower body elevator 120 of the full body elevator 101. The elevator cushion 140 may be foam rubber or other padded or flexible material. The elevator cushion 140 may be generally elongated and rectangular with a lower cushion surface 141 (FIG. 16) and an upper cushion surface 142. A transverse lower cushion surface notch 143 may be provided in the lower cushion surface 141 of the elevator cushion 140. A pair of transverse parallel, spaced-apart upper cushion surface notches 144 may be provided in the upper cushion surface 142 of the elevator cushion 140. Accordingly, as illustrated in FIG. 8, the lower cushion surface notch 143 accommodates the bend or apex between the leg support panel 126 of the leg portion 121 and the foot portion 128 of the lower body elevator 120. As further illustrated in FIG. 8, the upper cushion surface notches 144 accommodate the bends between the backrest panel 113 and the butt rest panel 115 of the upper body elevator 102 and the butt rest panel 115 of the upper body elevator 102 and the leg support panel 126 of the leg portion 121 of the lower body elevator 120, respectively. Therefore, in the inflated configuration of the full body elevator 101, the elevator cushion 140 includes a cushion backrest portion 145 which rests on the backrest panel 113 of the upper body elevator 102; a cushion butt portion 146 which rests on the butt rest panel 115 of the upper body elevator 102; a cushion leg portion 147 which rests on the leg support panel 126 of the leg portion 121; and a cushion foot portion 148 which rests on the foot support panel 129 of the foot portion 128.

Figure 17:
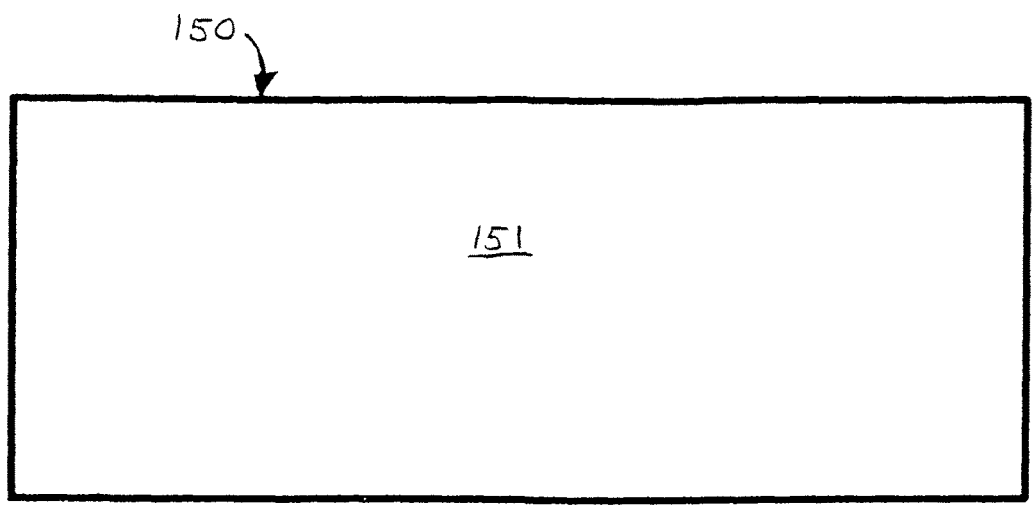
FIG. 17 is a top view of an elevator cover of an illustrative embodiment of the full body elevator.
Figure 18:
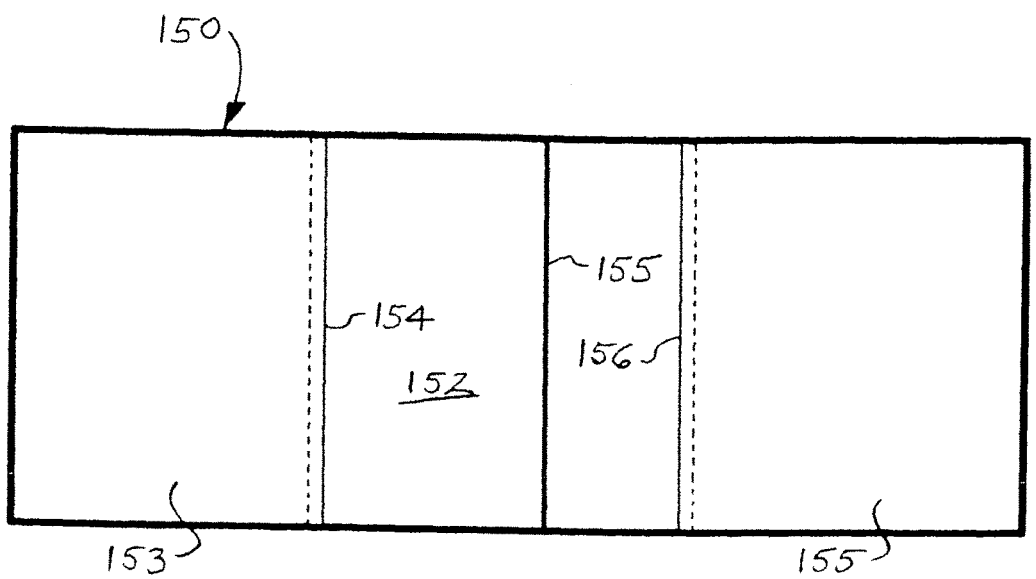
FIG. 18 is a bottom view of the elevator cover with the full body elevator (not illustrated) enclosed in the elevator cover.

As illustrated in FIGS. 17 and 18, in some embodiments, an elevator cover 150 may contain, enclose or envelope the upper body elevator 102 and the lower body elevator 120. The elevator cover 150 may be cotton, polyester or other suitable material with an upper cover panel 151 (FIG. 17) and a lower cover panel 152 (FIG. 18). An upper body elevator pocket 153 having a pocket opening 154 and a lower body elevator pocket 155 having a pocket opening 156 are provided in the lower cover panel 152 of the elevator cover 150. Accordingly, the upper body elevator pocket 153 receives and accommodates the upper body elevator 102 and the lower body elevator pocket 155 receives and accommodates the lower body elevator 120 of the full body elevator 101. The pocket openings 154, 156 may be sewn, stitched or otherwise closed to enclose and secure the upper body elevator 102 and the lower body elevator 120 in the elevator cover 150.

As illustrated in FIGS. 7-9, in exemplary application, the full body elevator 101 may initially be deployed or maintained in a deflated configuration, as illustrated in FIG. 7, for storage and/or transportation purposes. The upper body elevator 102 and the lower body elevator 120 can be selectively inflated, as illustrated in FIGS. 8 and 9, to comfortably support the upper body and the lower body (not illustrated), respectively, of a user of the full body elevator 101 as the user reclines on the elevator cushion 140. The upper body elevator 102 can be selectively inflated by coupling an air pump (not illustrated) to the air inlet valve 110 and pumping air into the upper body elevator air compartments 109 (FIG. 10). Accordingly, in the inflated upper body elevator 102, as illustrated in FIGS. 8 and 9, the backrest panel 113 slopes downwardly and the butt rest panel 115 is horizontal.

The leg portion 121 of the lower body elevator 120 can be selectively inflated by coupling an air pump to the air inlet valve 127 and pumping air into the leg portion air compartments 125 (FIG. 11). The foot portion 128 of the lower body elevator 120 can remain deflated, as illustrated in FIG. 8, to support the legs of the user in a lowered position. Alternatively, the foot portion 128 of the lower body elevator 120 can be selectively partially or fully inflated, as illustrated in FIG. 9, to support the feet (not illustrated) of the user in an elevated position according to the preferences of the user. The foot portion 128 can be selectively inflated by coupling an air pump to the air inlet valve 135 (FIG. 9) and pumping air into the foot portion air compartments 132 (FIG. 11). The full body elevator 101 can be selectively deflated (FIG. 7) by opening the air valves 110, 127 and 135 and allowing air to escape from the upper body elevator 102 and the lower body elevator 120.

While illustrative embodiments of the disclosure have been described above, it will be recognized and understood that various modifications can be made in the disclosure and the appended claims are intended to cover all such modifications which may fall within the spirit and scope of the disclosure.

What is claimed is:

1. A full body elevator, comprising:
an inflatable upper body elevator having a sloped backrest panel and a generally flat, horizontal butt rest panel extending from said backrest panel; and
an inflatable lower body elevator having a leg portion with a leg support panel sloping from said butt rest panel and a foot portion with a foot support panel selectively inflatable and extendable with respect to said leg portion, said foot portion selectively inflatable to deploy said foot support panel between a downwardly-sloped lowered position relative to said leg support panel of said leg portion and a horizontal raised position.

2. The full body elevator of claim 1 wherein said upper body elevator and said lower body elevator are separately inflatable.

3. The full body elevator of claim 1 wherein said leg portion and said foot portion of said lower body elevator are separately inflatable.

4. The full body elevator of claim 1 wherein said upper body elevator comprises a pair of upper body elevator side panels and said backrest panel is carried by said upper body elevator side panels.

5. The full body elevator of claim 4 wherein each of said pair of upper body elevator side panels is generally a right triangle.

6. The full body elevator of claim 1 wherein said leg portion of said lower body elevator comprises a pair of leg portion side panels.

7. The full body elevator of claim 6 wherein each of said pair of leg portion side panels is generally a scalene triangle.

8. The full body elevator of claim 1 wherein said foot portion of said lower body elevator comprises a pair of generally triangular foot portion side panels.

9. A full body elevator, comprising:
an inflatable upper body elevator having an upper body elevator bottom panel, a pair of upper body elevator side panels extending from said upper body elevator bottom panel, a sloped backrest panel carried by said upper body elevator side panels and a generally flat, horizontal butt rest panel extending from said backrest panel; and
an inflatable lower body elevator having a leg portion with a leg portion bottom panel, a pair of leg portion side panels extending from said leg portion bottom panel, a leg support panel carried by said leg portion side panels and sloping from said butt rest panel of said upper body elevator and a foot portion with a foot support panel selectively inflatable and extendable with respect to said leg portion, said foot portion selectively inflatable to deploy said foot support panel between a downwardly-sloped lowered position relative to said leg support panel of said leg portion and a horizontal raised position;
said leg portion including a plurality of adjacent leg portion air compartments and at least one air diffuser between said leg portion air compartments to facilitate flow of air between said leg portion air compartments; and
said foot portion including a plurality of adjacent foot portion air compartments and at least one air diffuser between said foot portion air compartments to facilitate flow of air between said foot portion air compartments.

10. The full body elevator of claim 9 wherein said upper body elevator and said lower body elevator are separately inflatable.

11. The full body elevator of claim 9 wherein said leg portion and said foot portion of said lower body elevator are separately inflatable.

12. The full body elevator of claim 9 wherein each of said pair of upper body elevator side panels is generally a right triangle.

13. The full body elevator of claim 9 wherein each of said pair of leg portion side panels is generally a scalene triangle.

14. The full body elevator of claim 9 wherein said foot portion of said lower body elevator comprises a pair of foot portion side panels and said foot support panel is carried by said foot portion side panels.

15. The full body elevator of claim 14 wherein each of said foot portion side panels is generally a right triangle.

16. A full body elevator, comprising:
   an inflatable upper body elevator having a sloped backrest panel and a generally flat, horizontal butt rest panel extending from said backrest panel;
   an inflatable lower body elevator having a leg portion with a leg support panel sloping from said butt rest panel and a foot portion with a foot support panel selectively inflatable and extendable with respect to said leg portion, said foot portion selectively inflatable to deploy said foot support panel between a downwardly-sloped lowered position relative to said leg support panel of said leg portion and a horizontal raised position;
   said leg portion including a plurality of adjacent leg portion air compartments and at least one air diffuser between said leg portion air compartments to facilitate flow of air between said leg portion air compartments;
   said foot portion including a plurality of adjacent foot portion air compartments and at least one air diffuser between said foot portion air compartments to facilitate flow of air between said foot portion air compartments; and
   an elevator cushion carried by said backrest panel and said butt rest panel of said upper body elevator and said leg support panel and said foot support panel of said lower body elevator.

17. The full body elevator of claim 16 further comprising an elevator cover substantially enclosing said upper body elevator and said lower body elevator.

18. The full body elevator of claim 17 wherein said elevator cover comprises an upper cover panel, a lower cover panel carried by said upper cover panel, an upper body elevator pocket in said lower cover panel and accommodating said upper body elevator and a lower body elevator pocket in said lower cover panel and accommodating said lower body elevator pocket.

19. The full body elevator of claim 16 further comprising a pair of cushion surface notches in a first surface of said elevator cushion and a cushion surface notch in a second surface of said elevator cushion.

20. The full body elevator of claim 16 wherein said leg portion and said foot portion of said lower body elevator are separately inflatable.

* * * * *